United States Patent
Madhavamenon et al.

(10) Patent No.: US 10,363,225 B2
(45) Date of Patent: Jul. 30, 2019

(54) NON-BLEEDING BIOACTIVE NATURAL PIGMENTS WHICH PREVENT COLOR AND DUST EXPLOSIONS, METHOD OF PREPARATION THEREOF

(71) Applicant: AKAY FLAVOURS & AROMATICS PVT LTD., Kerala (IN)

(72) Inventors: Krishnakumar Illathu Madhavamenon, Kerala (IN); Balu Paulose Maliakel, Kerala (IN)

(73) Assignee: Akay Flavours & Aromatics Pvt, Ltd (IN)

( * ) Notice: Subject to any disclaimer, the term of this patent is extended or adjusted under 35 U.S.C. 154(b) by 0 days.

(21) Appl. No.: 15/673,738

(22) Filed: Aug. 10, 2017

(65) Prior Publication Data

US 2018/0042858 A1 Feb. 15, 2018

(30) Foreign Application Priority Data

Aug. 11, 2016 (IN) .............................. 201641027492

(51) Int. Cl.
| | | |
|---|---|---|
| A61K 9/50 | (2006.01) | |
| A61K 36/9066 | (2006.01) | |
| A61K 31/12 | (2006.01) | |
| A61K 9/20 | (2006.01) | |
| A61K 9/16 | (2006.01) | |
| A61K 36/00 | (2006.01) | |

(52) U.S. Cl.
CPC .......... *A61K 9/5047* (2013.01); *A61K 9/1652* (2013.01); *A61K 9/1688* (2013.01); *A61K 9/1694* (2013.01); *A61K 9/2027* (2013.01); *A61K 9/2054* (2013.01); *A61K 9/2059* (2013.01); *A61K 9/2063* (2013.01); *A61K 9/2095* (2013.01); *A61K 9/5026* (2013.01); *A61K 9/5089* (2013.01); *A61K 31/12* (2013.01); *A61K 36/9066* (2013.01); *A61K 36/00* (2013.01); *A61K 2236/17* (2013.01); *A61K 2236/30* (2013.01)

(58) Field of Classification Search
CPC .............. A61K 36/9066; A61K 9/5047; A61K 9/5026; A61K 31/12; A61K 9/2095; A61K 9/5089; A61K 9/2027; A61K 36/00; A61K 2236/17; A61K 2236/30
See application file for complete search history.

(56) References Cited

U.S. PATENT DOCUMENTS

| 4,307,117 A | 12/1981 | Leshik | |
|---|---|---|---|
| 2006/0062881 A1* | 3/2006 | Berndt | A21D 2/36 426/549 |
| 2011/0274809 A1 | 11/2011 | Miuchi et al. | |
| 2011/0287085 A1 | 11/2011 | Kurzrock et al. | |
| 2013/0029905 A1* | 1/2013 | Madhavamenon | A61K 36/48 514/5.5 |
| 2014/0031403 A1 | 1/2014 | Gately et al. | |
| 2018/0028447 A1* | 2/2018 | Sezgin | A61K 9/167 |

FOREIGN PATENT DOCUMENTS

| EP | 2559347 A1 | 2/2013 | |
|---|---|---|---|
| EP | 2249852 B1 | 12/2014 | |
| JP | 08-187066 A | 7/1996 | |
| WO | WO-2014111956 A2 * | 7/2014 | ............. A61K 9/145 |

OTHER PUBLICATIONS

Fatemeh Zabihi, Na Xin, Sining Li, Jingfu Jia, Tao Cheng and Yaping Zhao, "Polymeric coating of fluidizing nano-curcumin via anti-solvent supercritical method for sustained release", The Journal of Supercritical Fluids, 89 (2014) 99-105. (Year: 2014).*
Shuxin Wan, Yingqian Sun, Xiuxiang Qi, and Fengping Tan, "Improved Bioavailability of Poorly Water-Soluble Drug Curcumin in Cellulose Acetate Solid Dispersion", AAPS PharmSciTech, vol. 13, No. 1, Mar. 2012. (Year: 2012).*
Vivek Ramshankar Yadav, Sarasija Suresh, Kshama Devi and Seema Yadav, "Novel formulation of solid lipid microparticles of curcumin for anti-angiogenic and anti-inflammatory activity for optimization of therapy of inflammatory bowel disease", Journal of Pharmacy and Pharmacology 2009, 61: 311-321. (Year: 2009).*
Krishnamurthy KS, Saji KV, Srinivasan V, Dinesh R, Tamil Selvan M and Anandaraj M (Eds.) 2011. Souvenir and Abstracts, National sympsoium on spices and aromatic crops (SYMSAC VI): Exploiting spices production potential of the Deccan region, Indian Society for Spices, Kozhikode, Kerala, India. (Year: 2011).*
Hesham Abdul Aziz, Kok Khiang Peh & Yvonne Tze Fung Tan, "Solubility of Core Materials in Aqueous Polymeric Solution Effect on Microencapsulation of Curcumin", Drug Development and Industrial Pharmacy, 2007, 33:11, 1263-1272. (Year: 2007).*
Aggarwal, et al., "Curcumin Derived from Turmeric (*Curcuma longa*): a Spice for All Seasons," *Phytopharmaceuticals in Cancer Chemoprevention*, Chap. 23, pp. 349-387 (2004).

(Continued)

*Primary Examiner* — John Pak
*Assistant Examiner* — Nathan W Schlientz
(74) *Attorney, Agent, or Firm* — Brinks Gilson & Lione; Ryan L. Marshall; Jonathan Hartley

(57) ABSTRACT

A non-bleeding curcumin (NBC) which eliminate the problems of color bleeding, color leaching, color staining and dusting during the industrial processing of curcumin and its methods of preparation is disclosed in the invention. The invention also provides a water based process of preparation of food grade non-bleeding curcumin which is free of synthetic excipients.

6 Claims, 3 Drawing Sheets

(56) References Cited

OTHER PUBLICATIONS

Gadow, et al., "Comparison of the antioxidant activity of rooibos tea (*Aspalathus linearis*) with green, oolong and black tea," *Food Chemistry*, 60(1):73-77 (1997).
Kaefer, C.M., et al., The Role of Herbs and Spices in Cancer Prevention, *J. Nutr. Biochem.*, 19(6):347-361 (2008).
Marcocci, et al., "Antioxidant action of *Ginkgo biloba* extract EGb 761," *Methods Enzymol*, 234:462-475 (1994).
Ramaswamy, K., et al., "Neuroprotection by Spice-Derived Nutraceutials: You Are What You Eat!" *Mol. Neurobiol.*, 44(2):142-159 (2011).
Rice-Evans, et al., "Total antioxidant status in plasma and body fluids," *Methods Enzymol.*, 234:279-293 (1994).
Nirmala, C et al.,"Effect of curcumin on certain lysosomal hydrolases in isoproterenolinduced myocardial infarction in rats," *Biochem Pharmacol*, 51(1):47-51 (1996).
Funk, J.L et al., "Turmeric Extracts Containing Curcuminoids Prevent Experimental Rheumatoid Arthritis," *J Nat Prod*, 69(3): 351-355 (2006).
Deodhar, S.D et al., "Preliminary study on antirheumatic activity of curcumin (diferuloyl methane)," *Indian J Med Res*, 71:632-634 (1980).
Holt, P.R et al., "Curcumin Therapy in Inflammatory Bowel Disease: A Pilot Study," *Digestive Diseases and Sciences*, 50(11):2191-2193 (2005).
Arun N. et al., "Efficacy of turmeric on blood sugar and polyol pathway in diabetic albino rats," *Plant Foods for Human Nutrition*, 57: 41-52 (2002).
Aggarwal B.B et al., "Anticancer Potential of Curcumin: Preclinical and Clinical Studies," *Anticancer Research*, 23: 363-398 (2003).
Dorai T et al., "Role of chemopreventive agents in cancer therapy," *Cancer Letters*, 215: 129-140 (2004).
Hsu Chih-Hung et al., "Clinical studies with curcumin," *Advances in Experimental Medicine and Biology*, 470-480 (2007).
Kunnumakkara A.B. et al., "Curcumin inhibits proliferation, invasion, angiogenesis and metastasis of different cancers through interaction with multiple cell signaling proteins," *Cancer Letters*, 269: 199-225 (2008).
Ruby A.J. et al., "Anti-tumour and antioxidant activity of natural curcuminoids," *Cancer Letters*, 94:79-83 (1995).

\* cited by examiner

NON-BLEEDING BIOACTIVE NATURAL PIGMENTS WHICH PREVENT COLOR AND DUST EXPLOSIONS, METHOD OF PREPARATION THEREOF

FIELD OF THE INVENTION

The present invention relates to the non-bleeding forms of natural pigment compositions in particular to the non-bleeding curcumin powder, granule or beadlet forms of varying particle size and its process of preparation which eliminate the problems of color bleeding, color leaching, color staining and dusting during the industrial processing of curcumin. The invention also relates to the process of preparation of food grade non-bleeding/non-leaching curcumin employing preferably, but not limited to, natural ingredients or its derivatives.

BACKGROUND OF THE INVENTION

Turmeric (*Curcuma longa* L.), belonging to the family of Zingiberaceae, is a perennial herb native to India where its rhizome is used as a yellow colorant curry spice and traditional medicine. The active principle in turmeric was identified as a group of polyphenolic compounds, namely curcumin (74-78%), demethoxycurcumin (15-18%) and bis-demethoxycurcumin (4-6%) commonly referred to as 'curcumin' (Aggarwal et al., chap. 23, *Phytopharmaceuticals in Cancer Chemoprevention*, 2004). It is one of the well-studied natural molecules and considered as one of the world's most important herbal extract.

Observational studies have already delineated the dietary intake of turmeric with a reduced incidence of chronic diseases such as Cancer and Alzheimer's in the subcontinent of India (C. M. Kaefer et al. *J. Nutr. Biochem.*, 2008, 19, 347-361, K. Ramaswamy et al., *Mol. Neurobiol.*, 2011, 44, 142-159). Turmeric is used as a dietary spice, coloring agent in foods and textiles, and a treatment for a wide variety of ailments. It is widely used in traditional Indian medicine to cure biliary disorders, anorexia, cough, diabetic wounds, hepatic disorders, rheumatism, and sinusitis. Besides flavouring food, turmeric is used to purify the blood and skin conditions. In Ayurvedic cooking, turmeric is used everywhere, this multifaceted wonder spice helps to detoxify the liver, balance cholesterol levels, fight allergies, stimulate digestion, boost immunity, enhance complexion and also used as a natural antioxidant. Ayurveda recognizes turmeric as a heating spice, contributing bitter, pungent and astringent tastes. Turmeric treats the whole Gastro-Intestinal system. In general turmeric is used for weak stomachs, poor digestion, dyspepsia, to normalize metabolism and enhance the ability of stomach to withstand digestive acids. Turmeric is a great carminative, able to calm an upset digestive system by getting rid of gas trouble and distension.

Modern scientific research has identified and characterized curcuminoids as the main bioactive principle in turmeric rhizomes, as responsible for majority of its pharmacological effects including antioxidant, anti-inflammatory, anticancer, anti-alzheimers, neuroprotective, gastroprotective, anti-bacterial and antithrombotic effects.

Most of the research with respect to curcumin is to find the pharmacological activities and mechanisms of action and bioavailability. Poor oral bioavailability has been demonstrated as the major problem which limits the transition of its therapeutic efficacy to the clinic. Hydrophobic and water insoluble curcumin undergo rapid biotransformations. Many patents and non-patent literatures are available on the methods to overcome the poor bioavailability of curcumin, but these documents are silent in discussing the methods to overcome hygienic process difficulties due to its color staining and dusting of the yellow pigment "curcumin".

US 2011/0287085 A1: This invention provides a liposomal curcumin for treatment of cancer. The invention discloses compositions and methods for the treatment of cancer, including pancreatic cancer, breast cancer and melanoma, in a human patient. The methods and compositions of disclosed in this invention employ curcumin or a curcumin analogue encapsulated in a colloidal drug delivery system, preferably a liposomal drug delivery system. Suitable colloidal drug delivery systems also include nanoparticles, nanocapsules, microparticles or block copolymer micelles. However, this document is silent in discussing the process difficulties or bulk handling difficulties due to color explosion and dusting characteristics of curcumin.

US 2011/0274809 A1: This invention describes a method for masking curcumin flavour comprising mixing curcumin with a modified starch, however no information is available regarding on prevention color leaching of curcumin.

U.S. Pat. No. 4,307,117 A: This invention discloses a process to stabilize curcumin against color changes by maintaining the curcumin itself at low, stable pH values, while not upsetting the pH balance of a dry food mix which may be placed in contact therewith. Preferably, the pH of the curcumin is maintained at a value within the range of from about 3.5 to about 4.5, and comprises a spray-dried intimate mixture of curcumin, an organic acid, a buffer, a dispersant for the curcumin, and a film-forming encapsulant. A preferred use of the colorant is in dry mixes for instant puddings which are alkaline due to the salts employed to cause setting. However this record fails to teach ways to prevent the color leaching of curcumin by this method.

EP 2559347 A1: This invention describes a method for masking the pungent flavor of curcumin to obtain a preparation that can be taken without resistance. However no information is available regarding the prevention of color leaching of curcumin by this method.

JP 08-187066 A: This invention describes granular *curcuma longa* tea and its production. Sterilized *curcuma longa* is dried in the sun, dried in an atmosphere of hot air at 40-50° C. for 4-6 hours, further redried in an atmosphere of hot air at 65-75° C. for 8-12 hours and ground into a granular state to give the objective granular *Curcuma longa* tea. The *Curcuma longa* tea is preferably mixed with an herb which is dried and granulated or made into small pieces. However, no information is available regarding the prevention of color leaching of curcumin by this method.

EP 2249852 B1: This invention discloses stable water-soluble formulations of curcumin which make possible the manufacture of pharmaceutical and nutraceutical formulations of curcumin. However, no information is available regarding the prevention of color leaching of curcumin by this method.

US 2014/0031403 A: Describes forms of curcumin and the pharmaceutical compositions thereof. The forms of curcumin disclosed herein are curcumin polymorph Form III, curcumin-2-aminobenzimidazole co-crystal, and curcumin-L-lysine co-crystal. However this record does not teaches the prevention of color leaching or dusting of curcumin.

Amongst nutraceuticals and dietary supplements, curcumin supplements, especially tablets in enteric-coated forms and sustained release forms have been reported. Similarly, various encapsulation techniques to provide water dispersible, water soluble, stable and enhanced bioavailable formulations of curcumin are mentioned with relatively low amount of curcumin content ranging from 1 to 40% (w/w) or preferably from 10 to 20% (w/w). However no information on process difficulties or bulk handling difficulties due to color explosion and dusting or methods to produce curcumin powder, granules or beadlets containing not less than 90% curcuminoids without colour bleeding issues are described in the prior-arts.

Various methods for making curcumin from dried turmeric rhizome are known in the past. It generally involves preparation of oleoresins from turmeric rhizome by flaking, solvent extraction, and evaporation techniques. The oleoresin further undergoes crystallization and centrifugation to get wet cake. Dried cakes are then pulverized to prepare curcumin powder. The powder form is either used as such or perform granulation to modulate its density or flow properties suitable for capsules, tablets etc. However, no information to address the process difficulties or bulk handling difficulties of curcumin due to the color explosion and dusting characteristics have been discussed though it is a major issue of the curcumin processing industry.

Further, the color leaching or curcumin stains make the GMP production of curcumin products troublesome, expensive and non-hygienic. Once curcumin is produced, the entire plant need complete change over cleaning and it is done very often using organic solvents which makes the process and products expensive, time consuming and non-hygienic.

Hence there exists a long felt and unmet need to develop a green process to prepare curcumin powder and granule forms which can eliminate the problems discussed above, caused by color bleeding, dusting and staining characteristics of curcumin, without losing its biological effects.

OBJECTS OF THE INVENTION

The main object of the present invention is to provide curcumin, the yellow color pigment of turmeric rhizomes, in a form which is non-bleeding, without color leaching or staining and dust problems during industrial processing.

Another object of the present invention is to provide a process for the preparation of non-bleeding curcumin which can also be extended to various formulations of curcuminoids without losing its bioactivity.

Yet another object of the invention is to provide a 100% food-grade non-bleeding curcumin formulation suitable for various operations such as but not limited to granulation, blending, capsule filling, tableting, storage, springing, direct compression etc. without color explosion. Other objects of the invention will be apparent from the description of the invention herein below.

SUMMARY OF THE INVENTION

The present invention provides a non-bleeding curcumin which can solve the problems of color bleeding and dusting in various industrial processing environments and the process of preparing non-bleeding curcumin thereof.

In one aspect, the invention relates to a Non-bleeding curcumin (NBC) comprising curcumin and a coating of polymer, wherein the polymer is selected from the group consisting of a biopolymer (naturally occurring), synthetic polymer or a mixture thereof.

In another aspect, the invention provides a Non-bleeding curcumin (NBC) comprising all the three biologically active curcuminoids namely curcumin, demethoxycurcumin and bisdemethoxycurcumin in substantially the similar ratio as of standard curcumin.

In another aspect, the invention provides non-bleeding curcumin in the form of powder, granules, pellets, micropellets, beads, and beadlets having the particle size distribution in the range of 120 to 2000 microns.

In another aspect, the invention, the non-bleeding curcumin according to the present invention can be used in bioavailable formulation such as tablets, capsules along with other excipients. Non-bleeding curcumin (NBC) contains enhanced concentration of curcuminoids and prevents color leakage, bleeding, staining or dusting during industrial processing of curcumin.

In another aspect, the invention provides a process for preparation of Non-bleeding curcumin (NBC) comprising the steps:

a) preparation of oleoresins from dried turmeric rhizomes by flaking, solvent extraction and evaporation to get a crude pasty mass, hereinafter referred to as crude oleoresin;

b) crystallization and centrifugation of the crude oleoresins obtained in step a) to obtain wet cakes of oleoresin;

c) drying the wet cakes of oleoresin to obtain curcumin;

d) coating curcumin with—polymers by fluid bed coating techniques or employing blenders like ribbon blender or using pan coaters, wherein the polymer is selected from the group consisting of a biopolymer, synthetic polymer or a mixture thereof.

The invention also provides the process for the preparation of food grade non-bleeding curcumin comprising coating curcumin powder with biopolymer selected from the group consisting of cellulose, shellac, galactomannans, glucomannans, arabinoxylans, natural gums, proteins or a mixture thereof which is 100% food grade and free of synthetic excipients.

Various objects, features, aspects and advantages of the inventive subject matter will become more apparent from the following detailed description of preferred embodiments, along with the accompanying drawing figures.

BRIEF DESCRIPTION OF THE DRAWINGS

For a better understanding of the invention, few embodiments are described below with reference to the accompanying drawings, purely by way of example and non-limiting in which.

DETAILED DESCRIPTION OF THE INVENTION

Figure 1A:
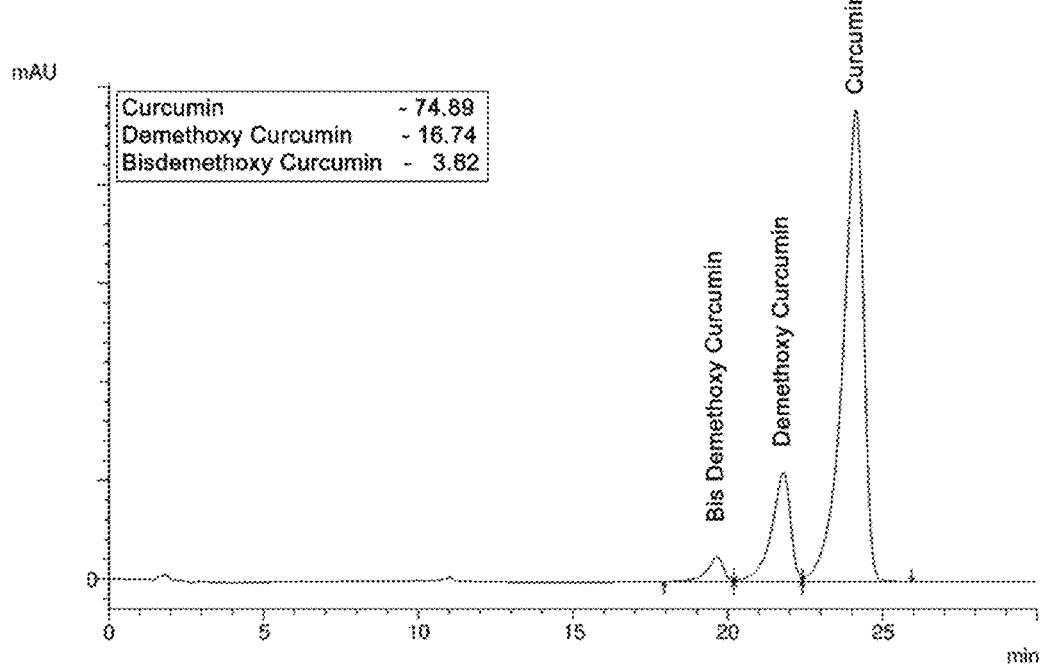
FIG. 1A illustrates content of three curcuminoids (curcumin, demethoxycurcumin and bisdemethoxycurcumin) of standard curcumin with 95% purity in % w/w (herein after referred to as 'standard curcumin') using HPLC.

A Non-bleeding Curcumin (NBC) comprising a curcumin and a coating of polymer and its process of preparation is presented. In the following description, for the purpose of explanation, numerous specific details are set forth to provide a thorough understanding. It may be apparent to one skilled in the art and domain that such specific details are not necessary to practice the invention. In other instances, diagrams and examples are provided to avoid obscuring details. In the specification and the claims the non-bleeding curcumin, non-bleeding curcumin (NBC) and NBC represent the same.

The term "standard curcumin" refers to curcumin with 95% purity that has all three curcuminoids i.e. curcumin, demethoxycurcumin and bisdemethoxycurcumin.

In an embodiment, the present invention provides a non-bleeding curcumin (NBC) comprising curcumin and a coating of polymer, wherein the polymer is selected from the group consisting of a biopolymer, synthetic polymer or a mixture thereof.

In one embodiment of the invention, the biopolymer is selected from the group consisting of cellulose, shellac, galactomannans, glucomannans, arabinoxylans, natural gums, proteins and the synthetic polymers is selected from the group consisting of polyvinyl alcohol, poly lactic acids among others. In some embodiments, the polymer is selected depending on the end applications of the curcumin.

In an embodiment, cellulose is selected from the group consisting of, but not limited to hydroxypropyl cellulose, hydroxypropyl methylcellulose, microcrystalline cellulose, cellulose ethers, methylcellulose, hydroxyethyl cellulose, cyclodextrins and other semisynthetic derivatives of cellulose or starch having a film forming capacity. In an embodiment the naturally occurring biopolymers consisting of, but not limited to galactomannans obtained from fenugreek, guar gum, psyllium seeds and glucomannans from amorphophallu, konjac, tamarind gum and similar suitable biopolymers.

In another embodiment the non-bleeding curcumin comprises all the three biologically active curcuminoids namely curcumin, demethoxycurcumin and bisdemethoxycurcumin in substantially the similar ratio as of standard curcumin.

In accordance with yet another embodiment of the invention, the non-bleeding curcumin can be in the form of powder, granules, pellets, micropellets, beads, and beadlets and can be produced with different particle size distribution and density suitable for various applications.

In some embodiments, the non-bleeding curcumin (NBC) according to the present invention is in the form of a uniform granules, generally beadlet shape, and the granules provides excellent free flowing characteristics, which are very desirable for manufacturing and formulating operations.

The non-bleeding curcumin (NBC) in the form of granules is convenient to use, and has a stronger visual appeal. Further the NBC granules of the present invention also have barriers to prevent penetration of light, moisture and/or air. The granules of the present invention are well suited for use as directly compressible ingredients in tablets, or in two-piece capsules.

In a still another embodiment of the invention, the non-bleeding curcumin (NBC) has particle size distribution in the range of 120 to 2000 microns. The size of the beadlets of the present invention may range between 250 microns and 841 microns, more preferably about 250 microns to about 420 microns.

The non-bleeding curcumin according to the present invention possess significant health beneficial effects and bioactivities.

In another embodiment of the invention, the non-bleeding curcumin (NBC) can be used in bioavailable formulation such as tablets, capsules along with other excipients.

In yet another embodiment of the invention, the non-bleeding curcumin (NBC) contains enhanced concentration of curcuminoids, preferably not less than 90% (w/w) and more preferably up to 95% (w/w) suitable for various formulations or bioavailable formulations.

In a still another embodiment of the invention, the non-bleeding curcumin (NBC) prevents color leakage, bleeding, staining or dusting during industrial processing of curcumin including the operations such as blending, capsule filling, tableting, storage, springing, direct compression among others.

The invention provides a non-bleeding curcumin, which prevents dust explosion and spreading of curcumin particles in a processing plant, avoids color staining on contact surfaces including machineries, plant facilities, worker accessories including dress, head gear, footwear, etc. thus minimizing the cost associated with cleaning.

In some embodiments, the non-bleeding curcumin reduces the chances of cross contamination with other materials, ingredients or equipment's used in processing plants.

In yet another embodiment of the present invention, the non-bleeding curcumin (NBC) retains radical scavenging property, biological activity, flavor, color and other properties of curcumin.

The non-bleeding curcumin eliminates the need of storage in cool, dry place or protected from sunlight, which will cause normal or standard or uncoated curcumin products to fade.

The non-bleeding curcumin enables flavour masking and flavour retention upon long term storage, as the NBC according to the invention will not volatilize and dissipate its aromatic essential oil under mild hot conditions.

The non-bleeding curcumin according to the invention resists the formation of cakes or lumps in a high humid processing environments or storage conditions.

The non-bleeding curcumin according to the invention increases the mechanical strength of the dosage forms.

In some embodiments the non-bleeding curcumin according to the invention can be used in various bioavailable formulations without losing the bioactivity.

In some embodiments the non-bleeding curcumin according to the invention prevents the colour leakage, bleeding or dusting of curcumin without masking and losing its natural characteristic yellow-orange color.

The non-bleeding curcumin according to the invention enhances the wettability of hydrophobic molecules like curcumin in water.

In an embodiment the present invention provides a process for the preparation of non-bleeding curcumin comprising coating curcumin with a polymer.

In an embodiment of the invention, the process for the preparation of NBC comprises coating curcumin with a polymer by bottom spray fluid bed drier or top spray fluid bed drier or employing blenders like ribbon blender or using pan coaters, wherein the polymer is selected from the group consisting of a biopolymer, synthetic polymer or a mixture thereof.

In an embodiment, curcumin used above can be obtained by any known method is the relevant art from turmeric rhizomes.

In accordance with another embodiment of the invention, the process of preparation of non-bleeding curcumin (NBC) comprises the steps of:

a) preparation of oleoresins from dried turmeric rhizomes by flaking, solvent extraction and evaporation;

b) crystallization and centrifugation of the crude oleoresin obtained in step a) to get wet cakes of oleoresin;

c) drying the wet cakes of oleoresin to obtain curcumin;

d) coating curcumin with polymer by bottom spray fluid bed drier or top spray fluid bed drier or employing blenders like ribbon blender or using pan coaters, wherein the polymer is selected from the group consisting of a biopolymer, synthetic polymer or a mixture thereof.

In an embodiment, preparation of oleoresins step a) comprises cutting dried turmeric rhizomes into pieces, flaking then followed by extraction using organic solvents, filtering and evaporating to obtain crude oleoresin rich in curcuminoids. The organic solvent can be any organic solvent suitable for the extraction process such as ethanol, ethyl acetate, acetone, acetone/hexane, dichloromethane or mixture thereof.

In an embodiment, the large scale evaporation may be carried out using various commercially available evaporators including, but not limited to thin film evaporators.

In an embodiment, crystallization step b) and drying step c) comprises providing crude oleoresin obtained in step a) in organic solvent(s), and isolating obtained crystals, then followed by washing and drying to obtain powder of curcumin with 80 to 97% purity, preferably 90 to 96%.

In yet another embodiment the curcumin obtained in step (c) which is in the form of powder is converted into granules by one of the granulation techniques selected from dry granulation, wet granulation or any other granulation method; and the powder is converted into beadlets by extrusion and spheronization method or any other known methods to the person skilled in the art.

In a still another embodiment of the invention, the biopolymer is selected from the group consisting of cellulose, shellac, galactomannans, glucomannans, arabinoxylans, natural gums, proteins and the synthetic polymers is selected from the group consisting of polyvinyl alcohol, polylactic acids among others.

The invention also provides a water based process for the preparation of food grade non-bleeding curcumin powder comprising coating with biopolymer selected from the group consisting of cellulose, shellac, galactomannans, glucomannans, arabinoxylans, natural gums, proteins or a mixture thereof.

In an embodiment of the invention, the food grade non-bleeding curcumin is 100% food grade and is free of synthetic excipients.

The process for the preparation of non-bleeding curcumin (NBC) according to the present invention can be used for preparation of non-bleeding pigments similar to curcumin including, but not limited to paprika extracts, carotenoids like lycopene, bixin, lutein, zeaxanthin, astaxanthin, capsanthin, capsnorubin, beta-carotene, chlorophyll, phycocyanins, spirulina extracts, anthocyanins, betalain, among others.

The non-bleeding curcumin (NBC) prepared according to the present invention were analyzed for curcumin content at stability conditions as mentioned below and found to be stable by retaining curcumin content. The Table 1 below outlines the physicochemical properties of NBC.

TABLE 1

Real time conditions: 40° C. ± 2° C./75% ± 5% RH.

| | | Non-bleeding curcumin (NBC) | | | | | | |
|---|---|---|---|---|---|---|---|---|
| Parameter | Specification | 0 month | 1 month | 2 month | 3 month | 4 month | 5 month | 6 month |
| Appearance | Golden yellow granules | Complies | Complies | Complies | Complies | Complies | Complies | Complies |
| Identification | HPLC | Complies | Complies | Complies | Complies | Complies | Complies | Complies |
| Odour | Characteristic | Complies | Complies | Complies | Complies | Complies | Complies | Complies |
| Curcumin content | NLT 92% | 92.18% | 92.18% | 92.17% | 92.17% | 92.17% | 92.16% | 92.16% |
| Residual solvent | NMT 25 ppm | Complies | Complies | Complies | Complies | Complies | Complies | Complies |
| Total heavy metal | <10 ppm | Complies | Complies | Complies | Complies | Complies | Complies | Complies |
| Microbiology | USFDA (BAM) | | | | | | | |
| Total plate count | <3000 cfu/g | 400 cfu/g | 400 cfu/g | 300 cfu/g | 300 cfu/g | 400 cfu/g | 500 cfu/g | 400 cfu/g |
| Yeast & Mould | <100 cfu/g | <10 cfu/g | <10 cfu/g | <10 cfu/g | <10 cfu/g | <10 cfu/g | <10 cfu/g | <10 cfu/g |
| Coliforms | <3 MPN/g | <3 MPN/g | <3 MPN/g | <3 MPN/g | <3 MPN/g | <3 MPN/g | <3 MPN/g | <3 MPN/g |
| E. Coli | Absent/g | Absent | Absent | Absent | Absent | Absent | Absent | Absent |
| Salmonella | Absent/25 g | Absent | Absent | Absent | Absent | Absent | Absent | Absent |

The NBC according to the present invention is tested for color leaching and showed no color leaching. The method for testing may be performed using any known method in the art or is mentioned in example 7.

Figure 1B:
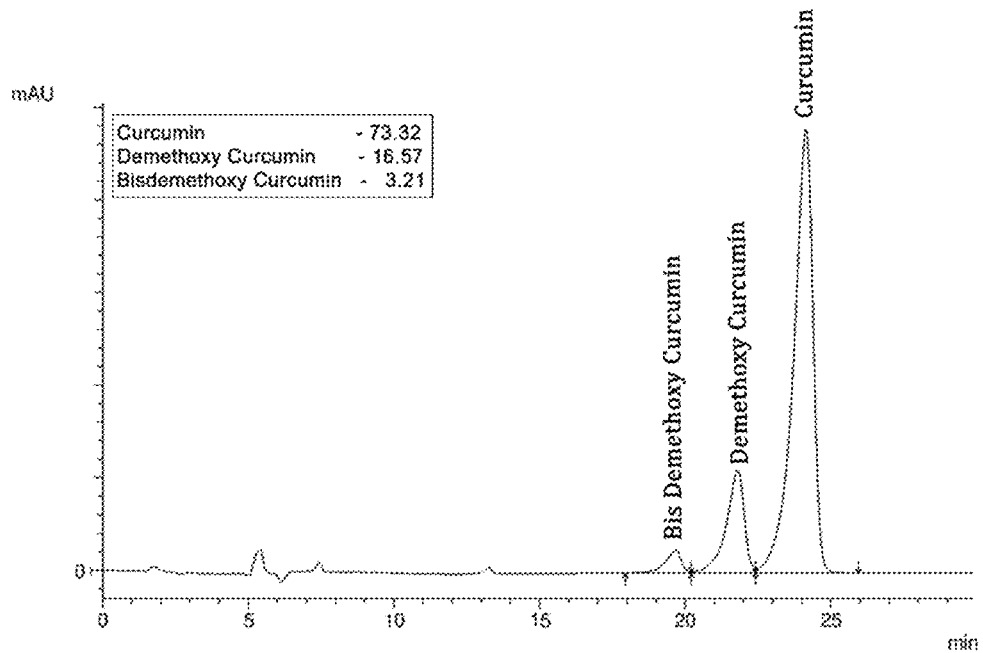
FIG. 1B illustrates content of three curcuminoids (curcumin, demethoxycurcumin and bisdemethoxycurcumin) of NBC in % w/w using HPLC.

The NBC according to the present invention showing no change in the content of all the three curcuminoids (curcumin, demethoxycurcumin and bisdemethoxycurcumin) compared to standard curcumin, is determined and confirmed by HPLC as shown in FIG. 1A and FIG. 1B.

The efficacy of NBC according to the present invention is tested against commonly used standard curcumin with 95% purity employing animal (rat) model to evaluate its bioavailability and absorption following oral administration. The results as shown in FIG. 2.

Figure 2:
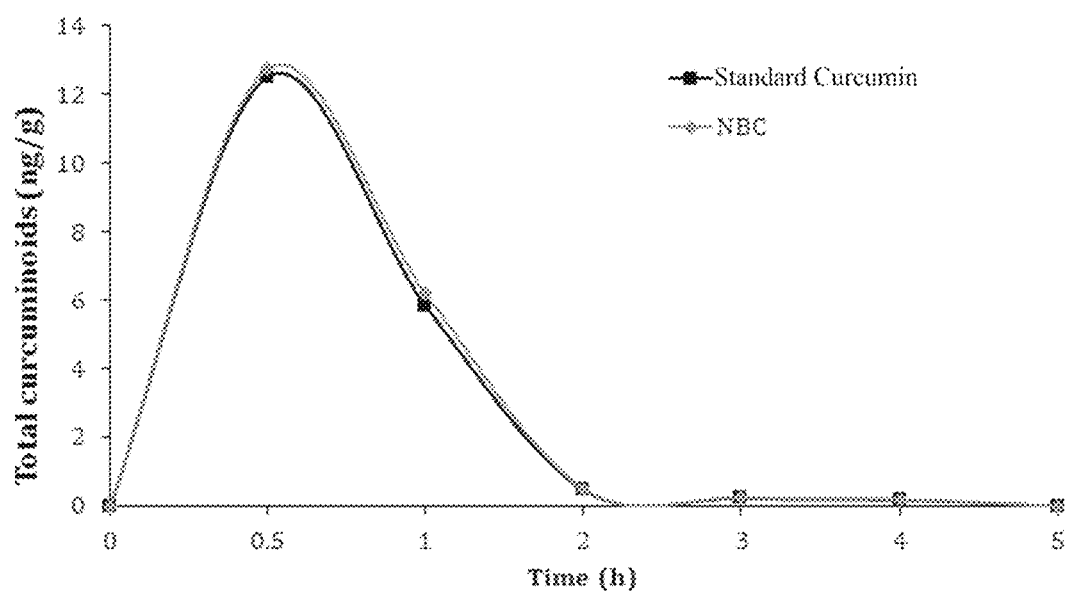
FIG. 2 illustrates efficacy (Bioavailability Studies) comparison of NBC and standard curcumin.

In FIG. 2, the average concentration of curcumin observed in rat plasma after oral administration of NBC and standard curcumin at 250 mg/kg dosage is shown. The data is expressed as mean±SD from n=16 rats used as two groups of eight animals each *p<0.05 and **p<0.01, (250 mg/kg NBC vs. 240 mg/kg standard curcumin with same curcuminoids content of 230 mg/kg b.wt.).

Figure 3:
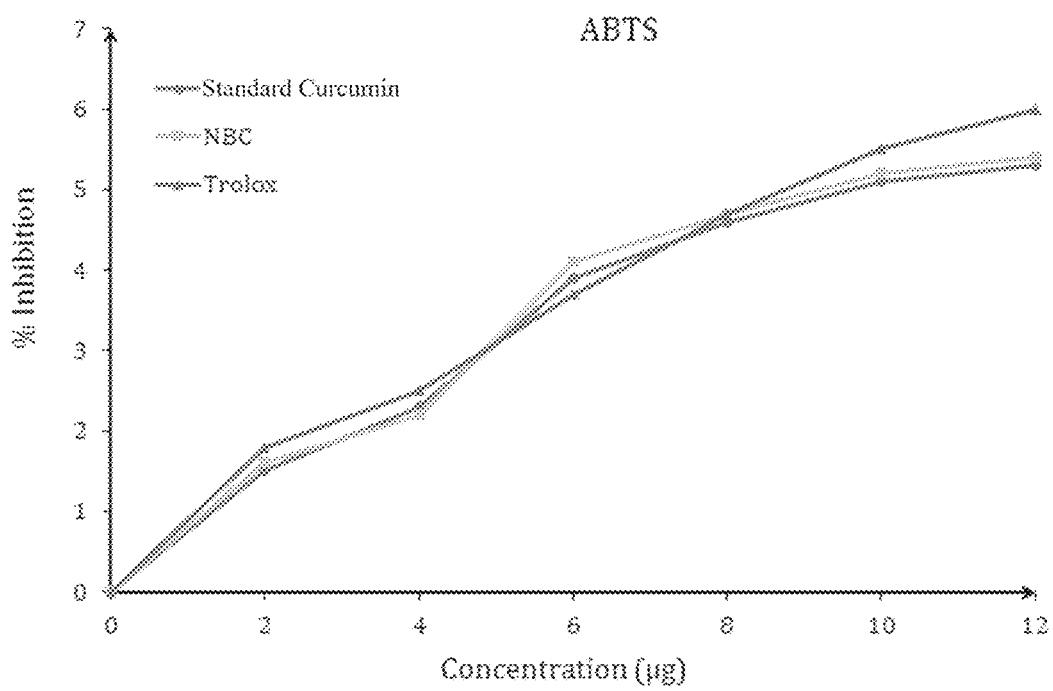
FIG. 3 illustrates comparison of ABTS (2,2'-azinobis (3-ethylbenzothiazoline-6-sulfonic acid) diammonium salt) radical scavenging assay of NBC and standard curcumin'.
Figure 4:
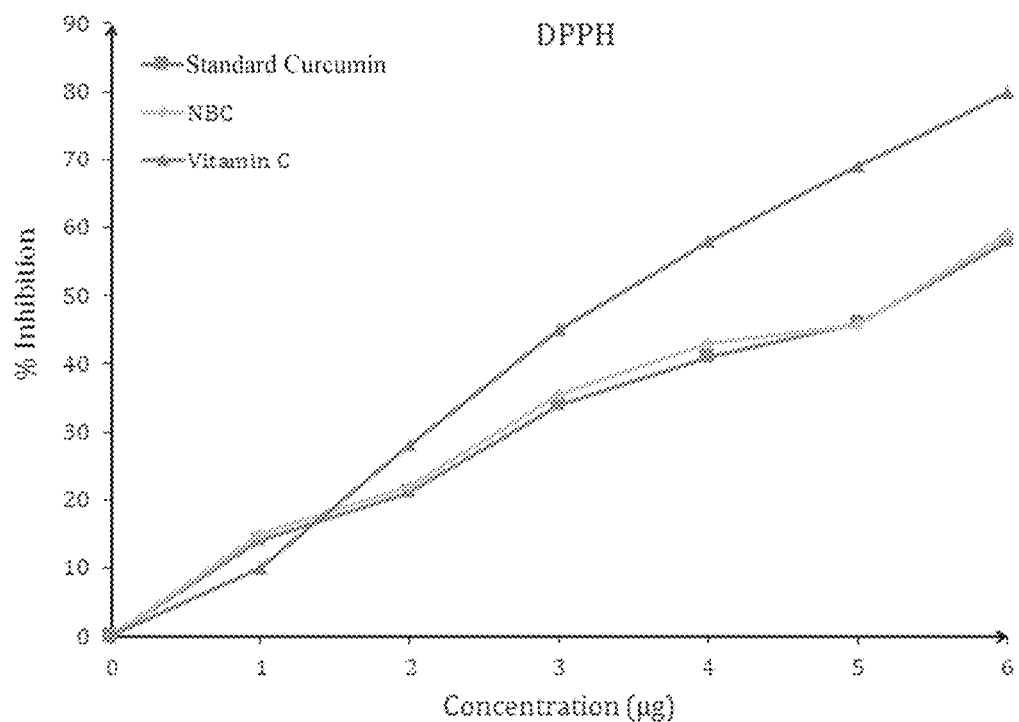
FIG. 4 illustrates comparison of DPPH (1,1-Diphenyl-2-picrylhydrazyl) radical scavenging assay of NBC and standard curcumin.
Figure 5:
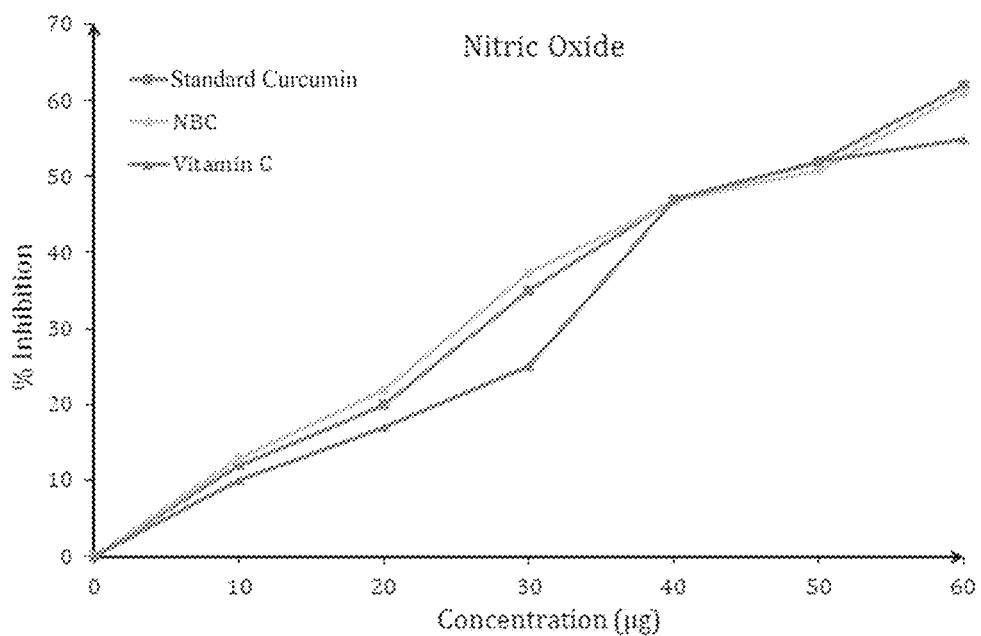
FIG. 5 illustrates comparison of Nitric Oxide radical scavenging assay of NBC and standard curcumin.

The radical scavenging property of NBC according to the present invention is retained and shown to be substantially equivalent to standard curcumin. In some embodiments, the radical scavenging properties that were retained are ABTS radical scavenging, DPPH radical scavenging, Nitric Oxide radical scavenging as shown in FIG. 3, FIG. 4 and FIG. 5 respectively. The exemplary example 10 details the few ways of estimating the scavenging activities.

In some embodiments, the radical scavenging activity of NBC according to present invention can be determined by using the ferryl myoglobin/ABTS protocol of Rice-Evans and Miller (1994) with minor modifications. (Rice-Evans et al, Methods Enzymol., 1994, 234, 279-293).

In some embodiments, the Nitric oxide scavenging activity of NBC according to present invention, can be estimated by the use of Griess reagent. Nitric oxide generated from sodium nitroprusside was measured by the Griess reagent by the method of Marcocci et al (1994). (Marcocci et al., Methods Enzymol 1994, 234: 462-475).

The DPPH (1,1diphenyl-2-picryl-hydrazyl) is a stable free radical and is known to be used as a model free radical compound to evaluate the effectiveness of antioxidants. The free radical scavenging activity of gallic acid (GA), or gallic acid-silver nanoparticle (SN-GA) complex was determined by method disclosed in Gadow et al., 1997, the same method is used to determine the radical scavenging of the NBC of the present invention, other methods known in the art can also be used. (Gadow et al., Food Chemistry, 1997; 60, 73-77).

The particle size is determined using sieve analysis (gradation test) to assess the particle size distribution of granular material. The typical sieve analysis involves a nested column of sieves with varied screen sizes. An accurately weighed sample is placed on the top sieve which has largest screen opening, where the sample moves from largest to smaller sieve openings. The mechanical shaker which hosts the sieve column, is operated for a specified time. The weight of the sample in each sieve is then divided by the total weight to give a percentage retained on each sieve. The size of the average particle on each sieve is then analyzed to get a cut-off point or specific size range.

The above description of the invention, together with the below accompanying examples should not be construed as limiting the invention because those skilled in the art to which this invention pertains will be able to devise other forms thereof within the ambit of the appended claims.

Example 1

Preparation of Curcumin 50 kg dried turmeric rhizomes having a curcumin content of 4.3% (w/w), were cut into small pieces using a stainless steel cutter and flaked to 2-3 mm size. It was then extracted using organic solvents such as ethanol, ethylacetate, acetone, acetone/hexane (mixture), or dichloromethane. The miscella (solvent+dissolved extract) was filtered and evaporated at 65-70° C. Further concentration under vacuum provided a thick pasty mass called oleoresin turmeric rich in curcuminoids.

10 kg of crude oleoresin was mixed with 30% w/v solvents like ethanol or isopropanol and allowed to settle. Yellow crystals of curcumin separated at the bottom was separated, washed and dried under vacuum to get dried yellow powder of curcumin with 80 to 97% purity. If required, crystallisation process was repeated to increase the purity, generally to higher than 92%.

Curcumin crystals thus produced can be ground under controlled conditions and sieved into various particle size fractions ranging from 10 to 100 mesh size (150 microns). Alternatively, fine powder of purified curcumin can also be granulated using the common practices of dry and wet granulation procedures. For example, curcumin powder with less than 80 mesh (180 microns) particle size can be passed through a roll compactor, followed by granulator to convert into granular form of curcumin with 95 to 97% curcumin content. In addition to compact granulation, high shear granulators, fluid bed granulators, extrusion/spheronization methods and other techniques can be used for making curcumin granules of varying sizes and shapes.

Example 2

Conversion of curcumin powder into standardized granular form of curcumin can be performed by any of the following process Wet Granulation 100 kg curcumin powder was loaded into a Mass Mixer and 20% aqueous ethanolic solution of hydroxypropyl cellulose was added to this powder. Both the solution and the curcumin powder were blended for some time. Unloaded and semidrying of the pieces was done in a tray drier. The semidried pieces were passed through the granulator. The 20 mesh pass particles dried to 90-100° C. Then sifted and collected between 20 and 60 mesh size. The powder passed through 60 mesh and the over size of 20 mesh were recycled.

Dry Granulation 30 kg curcumin powder was passed through roll compactor. The flakes collected were passed through the granulator. The 20 mesh pass particles were collected and sifted. Then it was passed through 60 mesh and the retained one was collected as product. The yield was 29.4 kg granular curcumin. The powder passed through 60 mesh and the over size of 20 mesh were recycled.

Extrusion and Spheronization 10 kg curcumin powder having a curcumin content of 95% was mixed with 50 g of microcrystalline cellulose and 800 g lactose. The mixture was passed through extruder and then passed through Spheronizer to obtain spheres. The sphere of curcumin has the curcumin content of 83%. Various food or pharma grade excipients can be used for spheronisation process.

Example 3

Preparation of Non-Bleeding or Non-Leaching Curcumin
 a) By bottom spray fluid bed coater
 b) By top spray fluid bed coater
 c) Employing blenders like ribbon blender
 d) Using pan coaters General fluid bed coating procedure: A particular quantity of uniform size granules was weighed and taken to the coating machine. The granulated curcumin was made and sieved to separate in various particle size. This was coated with cellulose based coating materials using spray gun. The coating mix was sprayed on to the inert granules present in a fluid-bed system provided with a bottom-spray mechanism at a temperature in the range of ambient temperature to about 45° C., at an atomisation pressure in the range of about 0.1 $kg/cm^2$ to about 3 $kg/cm^2$ with a spray rate in the range of about 10 g/hour to about 600 g/hour, and the resulting beadlets were dried at an atomisation pressure of about 0.8 kg/cm² to about 1.2 kg/cm². This coating will give protection against colour leaching. This product is available with a particle size of 20-40, 40-60 and 20-60 mesh. The curcumin content of the product is not less than 92%.

Curcumin beadlets prepared by extrusion and spheronization method can also be coated as specified above.

a) NBC by Bottom Spray 10 kg of uniform size (40-60 mesh) granules of curcumin with 95.1% purity was weighed and taken to the coating machine to coat with 2.1 liter of Hydroxypropyl methyl cellulose solution (2.5%). The coating material was sprayed on to the granules present in a fluid-bed system provided with a bottom-spray mechanism at a temperature in the range of 45 to 49° C., at an atmosphere pressure in the range of about 1.2 atmospheric pressure with a spray rate in the range of about 5-8 rpm. The said coating will give protection against colour leaching and the obtained product is available with a particle size of 20-40, 40-60 and 20-60 mesh. The curcumin content of the product is not less than 92.6%.

b) NBC by Top Spray

Top granulation can also be performed in a fluid-bed granulator.

10 kg of uniform size (40-60 mesh) granules of curcumin with 95.8% purity was weighed into the coating machine. It was coated with 2 liter of hydroxyl propyl cellulose solution (2.5%). The coating mix was sprayed on to the granules present in a fluid-bed system provided with a top-spray mechanism at a temperature in the range of 45 to 49° C., at an atmosphere pressure in the range of about 1.2 atmospheric pressure with a spray rate in the range of about 8-10 rpm. This coating will give protection against color leaching. This product is available with a particle size of 20-40, 40-60 and 20-60 mesh. The curcumin content of the product is not less than 93.3%.

c) Employing Blenders Like Ribbon Blender 4 kg of uniform size (40-60 mesh) granules of curcumin with 94.9% purity was weighed and taken to the ribbon blender and coated with 1.3 liter of Hydroxypropyl methyl cellulose solution (2.5%). The coating mix was sprayed on to the granules present in a ribbon blender. The curcumin content of the product is 92.4%.

Instead of Hydroxypropyl methyl cellulose, the same procedure above can be repeated with 1.6 liter of polyvinyl alcohol (2%) to produce non-bleeding curcumin.

d) Using Pan Coaters 4 kg curcumin spheres having a curcumin content of 92% was taken in a pan coater. While rotating the pan, 1.1 liter of Hydroxypropyl methyl cellulose solution (2.5%) was slowly sprayed on to the granules at 12-15 rpm with simultaneous blowing of hot air at 60° C. The beads were dried and sieved to get uniform non-bleeding curcumin particles. The curcumin content of this product is not less than 87%.

Example 4

Directly Compressible Beadlets of NBC 250 g of Non-bleeding granular curcumin (NBC) was mixed with starch (25 g), Magnesium stearate (5 g), Gelatine (25 g). After uniform blending the powder mixture was compressed into tablets of 550 mg weight with hardness of 7 kg/cm². There was only very little colour staining observed on contact surfaces including machineries, plant facilities, worker accessories including dress.

Alternatively, 250 g of standard curcumin was mixed with directly compressible grade excipients (cellulose, dextrose, mannitol and starch) and blended to uniform powder. It was wet by 10% (w/w) of water and dried. The dried cakes were milled to powder of 60-80 mesh size and were charged to a fluid bed granulator. It was then coated with HPMC solution as mentioned earlier in example 3. The resulting granular powder was pressed directly to get 500±30 mg tablets having a hardness of 7.3 kg/cm².

Example 5

Preparation and Evaluation of Tablet Formulation of Granules 250 g NBC beadlets were mixed with starch 25 g of starch, 5 g of magnesium stearate and 25 g of gelatin. After uniform blending the powder mixture was compressed into tablets of 550 mg weight with hardness of 7 kg/cm². This shows non-bleeding granular curcumin has required mechanical strength for tablets.

Example 6

Stability Studies

The beadlet formulations in the examples were subjected to stability studies at 40° C.±2° C./75%±5% RH (relative humidity). The results of the study is shown in Table 1.

The above study concludes that the beadlets prepared by the present invention provide adequate stability to the Curcuminoids.

The beadlets were analyzed for curcumin content before and after 6 months and it was found to be stable. The formulation is stable and have two year shelf-life.

Example 7

Colour Leaching Test 2 g of NBC was placed on the palm and the material was rubbed using finger against palm for 20 times to test its color leakage. It was observed that there was no color leaching or staining to the skin.

NBC prevents colour leakage, bleeding or dusting of curcumin without masking and losing its natural characteristic yellow-orange colour.

Example 8

Non-bleeding curcumin comprising all the three curcuminoids (curcumin, demethoxycurcumin and bisdemethoxycurcumin) with no change in the ratio of distribution determined and confirmed by HPLC (FIGS. 1A and 1B). Curcumin content was determined using HPLC method as below.

HPLC Method: Preparation of standard

The analytical standard of curcumin (CAS No: 458-37-7) was obtained from Sigma-Aldrich, Bangalore, India. On a microbalance weigh accurately 1.0+0.25 mg of curcumin and dissolved in methanol by sonication. The solution was then made up to 25 mL. Series of dilutions were prepared separately with acetone and a four point calibration was made.

Correct the curcumin stock standard concentration as follows:

[Curcumin mg/mL]corrected(stock)=[curcumin mg/mL]×purity

The standard stock solution is stable for one week when stored at 4-7° C.

Preparation of Sample

Weigh accurately 0.5 mg of the Curcumin sample into a 50 mL volumetric flask and makeup with Acetone. Pipet out 5 mL of this solution into 50 mL volumetric flask and dilute to volume. Filter through a 0.45 mm PTFE filter in to an amber auto sampler vial. It was injected to an HPLC fitted with a reverse phase C18 column using the mobile phase as 57:43 (v/v) mixture of 0.2% phosphoric acid containing water and acetonitrile. 20 mL of the sample was injected at a flow rate of 1.25 mL/min and the chromatogram was monitored at 420 nm. The column was at a constant temperature of 35±1° C.

Instrument Conditions
Column Temperature=35° C.
Detection=UV 420 nm
Flow rate=1.25 ml/minute
Injection volume=20 ml
Isocratic Run: 57.0% (0.2% Phosphoric acid in deionized/purified water 43.0% Acetonitrile
Run time=25 minutes
Retention time: Bis demethoxy curcumin—17.4
Demethoxycurcumin—19.3
Curcumin—21.5

% Curcuminoid=Area(sample)×[weight of the standard]÷Area(standard)×[weight of the sample]  Calculation

Example 9

Bioavailability Studies Employing Wistar Rats

Male Wistar albino rats 200-220 g body weight, were fasted overnight and received either standard curcumin or NBC orally as a suspension in aqueous solution containing 0.1% carboxymethyl cellulose, at a dose of 250 mg/kg body weight. Both NBC (curcumin content: 92%) and standard curcumin (curcumin content: 95%) were administered at same curcumin content level. The blood was collected after each time point, 0, 0.5, 1, 3, and 5 hours respectively into heparinized tubes and centrifuged at 6000×g for 15 minutes. Plasma was decanted and stored at −80° C. until HPLC analysis. 1 mL of plasma was extracted with 3×10 mL of ethyl acetate and was dried over anhydrous sodium sulphate and evaporated to dryness. The residue was then made up to 10 mL with methanol and 20 μL was injected to Shimadzu model LC-20 AT HPLC fitted with a PDA detector model M20A using a reverse phase C18 column (Phenomenex 250×4.6 mm, 511) and methanol mobile phase monitored at 420 nm. Measurement of curcumin content in plasma was validated by spiking a standard curcumin (CAS Registry No. 458-37-7) in animal blood and plasma at 1.0 μg/mL. Curcuminoid retention time was confirmed by repeated 10 analyses at 50 mg level on same column under identical conditions. Efficiency of extraction from blood and plasma was also confirmed by spiking 1 mg/mL standard curcumin. Range and linearity were determined for curcumin extracted from blood and plasma as mentioned above and the recovery of curcuminoids was calculated to be 89 and 91% respectively. The results are shown in FIG. 2.

Example 10

Free Radical Scavenging Activity Measurement
ABTS Radical Scavenging Assay

Reaction mixture (2 mL total volume) containing the following substances namely 150 μM ABTS (2,2'-azinobis (3-ethylbenzothiazoline-6-sulfonic acid) diammonium salt), 400 μM myoglobin, 740 μM potassium ferricyanide and 450 μM $H_2O_2$ were freshly prepared in distilled water. Metmyoglobin (MbIII) was made by mixing equal volumes of myoglobin and potassium ferricyanide solutions. The reaction was initiated by the addition of $H_2O_2$ (75 μM) and the reaction was measured at 734 nm. The % inhibition of ABTS radical was calculated from the slope obtained on the reaction progress.

$IC_{50}$ value of standard curcumin is 9.6 and NBC is 9.5 as shown in FIG. 3.

DPPH Radical Scavenging Assay

Freshly prepared methanolic solution of DPPH (1,1-Diphenyl-2-picrylhydrazyl) (634 μM) was incubated at ambient temperature with 0.2 mM GA or SN-GA and A515 was measured using a spectrophotometer. The percent of inhibition of DPPH reduction (decolourization) was calculated according to the formula, % of inhibition=(A0−A20)/A0×100.

IC 50 value of standard curcumin is 5.6 and NBC is 5.5 as shown in FIG. 4.

Nitric Oxide Radical Scavenging Assay

Various concentrations of extract and sodium nitroprusside in PBS (phosphate-buffered saline) was incubated at 25° C. in a volume of 3 mL for 150 minute. After incubation 0.5 mL was removed and diluted with 0.5 mL of Griess reagent (1% sulfanilamide, 2% $H_3PO_4$ and 0.1% N-(1-naphthyl) ethylenediamine dihydrochloride). The absorbance of the chromophore that formed during diazotization of the nitrite with sulfanilamide and subsequent coupling with Naphthylethylenediamine dihydrochloride was immediately read at 546 nm. The inhibition of Nitric Oxide generation was estimated by comparing the absorbance value of the control with that of test.

Inhibition of nitrite formation by the curcumin and the standard antioxidant ascorbic acid were calculated relative to the control. Inhibition data (percentage inhibition $IC_{50}$) were linearized against the concentrations of each extract and standard antioxidant. $IC_{50}$ which is an inhibitory concentration of each extract required to reduce 50% of the nitric oxide formation was determined.

$IC_{50}$ value of standard curcumin is 47 and NBC is 48 as shown in FIG. 5.

The NBC curcumin used in evaluating the antioxidant activity in above studies has a curcuminoid content of >91.1%.

The invention claimed is:

1. A Non-bleeding curcumin (NBC) consisting of curcumin and a coating of polymer, wherein
   the polymer is selected from the group consisting of hydroxypropyl methylcellulose, hydroxypropyl cellulose, polyvinyl alcohol and mixtures thereof;
   the NBC contains concentration of curcuminoids not less than 90% (w/w) and up to 95% (w/w) measured by HPLC, which is substantially equivalent to standard curcumin with 95% purity;
   the NBC having the particle size distribution in the range of 180 to 2000 microns;
   the NBC retains radical scavenging property, biological activity, flavor, and color of said standard curcumin;
   and the polymer prevents color leakage, bleeding, staining or dusting during industrial processing of said curcumin.

2. The non-bleeding curcumin of claim 1, wherein the concentration of curcuminoids is curcumin (73.32%), demethoxy curcumin (16.57%), and bisdemethoxy curcumin (3.21%) which is substantially the similar ratio as of said standard curcumin.

3. The non-bleeding curcumin of claim 1, wherein the NBC is in the form of powder, granules, pellets, micropellets, beads, or beadlets.

4. The non-bleeding curcumin of claim 1, wherein the curcumin is crystalline.

5. A process for preparation of the NBC of claim 1, comprising:
   a) preparation of oleoresins from dried turmeric rhizomes by flaking, extractions with a suitable organic solvent and evaporation;
   b) adding an organic solvent to the oleoresin followed by crystallization of said curcumin and centrifugation to get wet cakes;
   c) separating the curcumin crystals from the wet cakes and washing and drying to obtain curcumin crystals with 92-97% purity;
   d) optionally, grinding, milling or granulating the curcumin crystals to adjust particle size to 10 to 100 mesh; and
   e) coating the curcumin crystals with polymer by bottom spray fluid bed drier, top spray fluid bed drier, ribbon blender or pan coater to obtain said NBC, wherein the polymer is selected from the group consisting of hydroxypropyl methylcellulose, hydroxypropyl cellulose, polyvinyl alcohol and mixtures thereof;
   wherein the NBC contains 90-95% w/w curcuminoids;
   the NBC has a particle size distribution in the range of 180 to 2000 microns;
   the NBC retains radical scavenging property, biological activity, flavor, and color of standard curcumin with 95% purity; and
   the polymer prevents color leakage, bleeding, staining or dusting during industrial processing of said curcumin.

6. The process for preparation of NBC of 5, wherein the curcumin is converted into granules or beadlets or powder with desired particle size by grinding or milling, wherein the powder is converted into granules by one of the granulation techniques selected from dry granulation, wet granulation or any other granulation method; and the powder is converted into beadlets by extrusion and spheronization method.

* * * * *